United States Patent [19]

Cliffe et al.

[11] Patent Number: 5,194,439
[45] Date of Patent: Mar. 16, 1993

[54] N-(2,3-DIHYDRO-1,4-BENZODIOXINYL)-N-SUBSTITUTED AMINOPYRIDO-FUSED CYCLOALKANES

[75] Inventors: Ian A. Cliffe, Slough; Howard L. Mansell; Richard S. Todd, both of Burnham; Alan C. White, Englefield Green, all of England

[73] Assignee: John Wyeth & Brother Limited, Maidenhead, England

[21] Appl. No.: 765,282

[22] Filed: Sep. 25, 1991

Related U.S. Application Data

[62] Division of Ser. No. 505,957, Apr. 6, 1990, Pat. No. 5,075,303.

[51] Int. Cl.$^5$ .................... A61K 31/47; C07D 513/04
[52] U.S. Cl. .................... 514/299; 514/311; 514/312; 514/313; 546/112; 546/153; 546/155; 546/157; 546/158; 546/159; 546/171; 546/183
[58] Field of Search ............... 546/153, 155, 157, 158, 546/159, 171, 112, 183; 514/311, 312, 313, 299

[56] References Cited

U.S. PATENT DOCUMENTS 4,878,941 11/1989 Theodoris ................ 544/182 X
4,894,084  1/1990 Theodoris ................ 546/155 X

FOREIGN PATENT DOCUMENTS

| 82417 | 6/1988 | Australia . |
| 0000395 | 1/1979 | European Pat. Off. . |
| 0041488 | 12/1981 | European Pat. Off. . |
| 0236140 | 9/1987 | European Pat. Off. . |
| 0236930 | 9/1987 | European Pat. Off. . |
| 0270947 | 6/1988 | European Pat. Off. . |
| 3719924 | 5/1988 | Fed. Rep. of Germany . |
| 1463583 | 5/1977 | United Kingdom . |
| 2190376 | 11/1987 | United Kingdom . |

OTHER PUBLICATIONS

Ornstein, et al., "Molecular Models", Chem. Biol. Interactions, 30 (1980) 87-103.

Primary Examiner—Marianne M. Cintins
Assistant Examiner—Catherine Scalzo
Attorney, Agent, or Firm—George Tarnowski

[57] ABSTRACT

Pyridine derivatives of formula

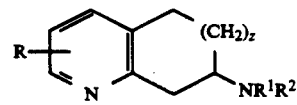

their heteroaromatic N-oxides and their pharmaceutically acceptable acid addition salts are disclosed. In the formula z is 0, 1 and 2; R is hydrogen, hydroxy, lower alkyl, lower alkoxy, halogen, trifluoromethyl, nitro, amino, (lower)alkylamino or di(lower)alkylamino; $R^1$ is hydrogen or lower alkyl; $R^2$ is $—(CH_2)_n—R^3$ or $—CH_2—CH=CH—(CH_2)_m—R^3$ or $—CH_2.C\equiv C.(CH_2)_m—R^3$ where n is 1 to 6, and m is 0 to 3; and $R^3$ is a ring of formula

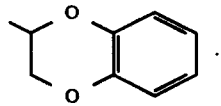

The compounds exhibit activity as 5-HT$_{1A}$ agonists, antagonists or partial agonists and are used for the treatment of CNS disorders, e.g. anxiety, as antihypertensives and in treating anorexia.

3 Claims, No Drawings

N-(2,3-DIHYDRO-1,4-BENZODIOXINYL)-N-SUBSTITUTED AMINOPYRIDO-FUSED CYCLOALKANES

This is a division of Application Ser. No. 07/505,957 filed Apr. 6, 1990 now U.S. Pat. No. 5,075,303.

This invention relates to pyridine derivatives, to processes for their preparation, to their use and to pharmaceutical compositions containing them. The novel compounds act on the central nervous system by binding to 5-HT receptors (as more fully explained below) and hence can be used as medicaments for treating humans and other mammals.

The compounds of the invention are those of formula

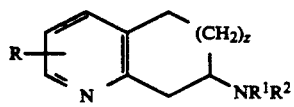
(I)

the heteroaromatic N-oxides thereof and the pharmaceutically acceptable acid addition salts of the compounds of formula (I) or the N-oxides. In the formula:

z is 0, 1 or 2;

R is hydrogen, hydroxy, lower alkyl, lower alkoxy, halogen, trifluoromethyl, nitro, amino, (lower)alkylamino or di(lower)alkylamino;

(A) $R^1$ is hydrogen or lower alkyl and $R^2$ is (a) hydrogen, (b) lower alkyl, or (c) —$CH_2)_n$—$R^3$ or —$CH_2$—CH=CH—$(CH_2)_m$—$R^3$ or —$CH_2.C≡C.(CH_2)_m$—$R^3$ where n is 1 to 6, m is 0 to 3 and $R^3$ (i) aryl; (ii) CN; (iii) $OR^4$ where $R^4$ is hydrogen, (lower) alkoxycarbonyl, aryl or aryl(lower)alkyl; (iv) $COOR^5$ where $R^5$ is hydrogen, lower alkyl or phenyl(lower)alkyl; (v) $CONR^{15}R^{16}$ where $R^{15}$ and $R^{16}$ are independently hydrogen, lower alkyl or phenyl(lower)alkyl; (vi) a ring of formula.

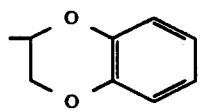

or (vii) a group of formula —$NR^6R^7$ where $R^6$ and $R^7$ are independently hydrogen, lower alkyl, aryl or aryl(lower)alkyl, or a group of formula —$COR^8$ or $SO_2R^9$ where $R^8$ is lower alkyl, lower alkoxy, aryl(lower)alkyl, aryl, adamantyl, heteroaryl, or —$NHR^{10}$ where $R^{10}$ represents hydrogen, lower alkyl, halo(lower)alkyl, aryl, aryl(lower)alkyl or heteroaryl and $R^9$ is lower alkyl, halo(lower)alkyl, (lower)alkoxycarbonyl(lower)alkyl, aryl or $NR^{11}R^{12}$ where $R^{11}$ and $R^{12}$ are independently, hydrogen, lower alkyl, aryl or aryl(lower)alkyl or $R^6$ and $R^7$ together with the nitrogen atom to which they are attached represent a group of the formula

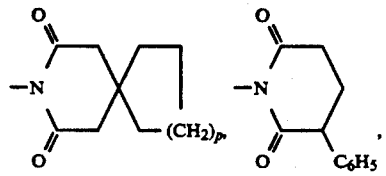

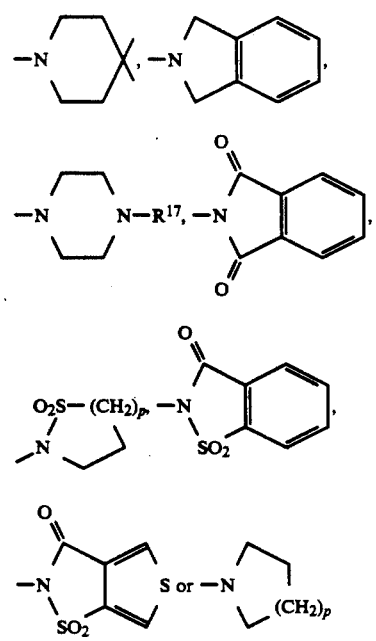

wherein p is 1 or 2 and $R^{17}$ is hydrogen, lower alkyl, aryl or aryl(lower)alkyl or (B) $R^1$ and $R^2$ together with the nitrogen atom to which they are attached represent a heterocyclic ring selected from

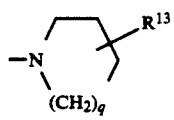

where q is 0, 1, 2 or 3 and $R^{13}$ is hydrogen, lower alkyl, hydroxy, lower alkoxy, amino, lower alkanoylamino or $COR^8$ where $R^8$ has the meaning given above;

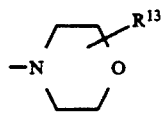

where $R^{13}$ has the meaning given above;

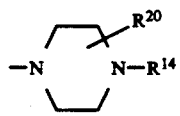

where R14 is hydrogen, lower alkyl, aryl, aryl(lower)alkyl, —$COR^8$ (where $R^8$ has the meaning given above) or

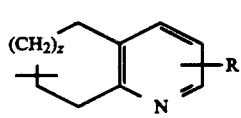

or (where R and z have the meanings given above) and $R^{20}$ is hydrogen, lower alkyl or lower alkoxy; and

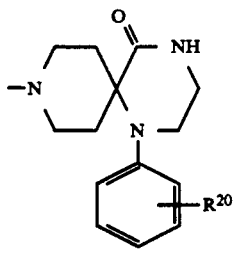

where $R^{20}$ has the meaning given above.

The term "lower" as used herein means that the radical referred to contains 1 to 6 carbon atoms. Preferably such radicals contain 1 to 4 carbon atoms. Examples of "lower alkyl" are methyl, ethyl, propyl, isopropyl, butyl, isobutyl, pentyl and isopentyl.

Examples of "lower alkoxy" are methoxy, ethoxy, propoxy, isopropoxy, butoxy, isobutoxy, pentoxy isopentoxy, hexoxy and isohexoxy.

Examples of "lower alkanoyl" include acetyl, propionyl and butyryl.

When used herein "aryl" means an aromatic radical having 6 to 12 carbon atoms (eg phenyl, naphthyl) which may optionally be substituted by one or more substituents selected from lower alkyl, lower alkoxy, halogen, trifluoromethyl, cyano, amino, (lower)alkylamino and di(lower)alkylamino. Examples of aryl(lower)alkyl radicals include benzyl, phenethyl and phenpropyl and triphenylmethyl.

When used herein "heteroaryl" means a 5 or 6 membered aromatic ring, containing oxygen, sulphur and/or nitrogen as hetero atom; the 5 or 6 membered aromatic ring may be fused to a further aromatic ring. The aromatic ring or rings may optionally be substituted by one or more lower alkyl, lower alkoxy, halogen, trifluoromethyl, amino, (lower)alkylamino or di(lower) alkylamino substituents. Examples of heteroaryl include optionally substituted furyl, pyridyl, pyrimidyl, quinolyl, benzimidazolyl and indolyl.

Preferred compounds of the invention are:
those in which z is 1;
those in which R is hydrogen; and
those in which $-NR^1R^2$ represents

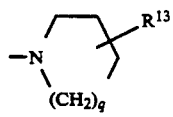

particularly those in which $-NR^1R^2$ represents an optionally substituted azetidino group The compounds of the invention may be prepared by reaction of a compound of formula

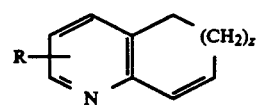

(where R and Z have the meanings given above) with an amine of formula $$NHR^1R^2 \qquad (III)$$

(where $R^1$ has the meaning given above and $R^2$ has the meaning of $R^2$ given above or is a precursor of the group $R^2$) or a protected form of the amine and, if necessary, converting any precursor group $R^2$ into a desired group $R^2$ and/or removing any protecting group. The reaction is a Michael type reaction which may be carried out in presence of an acid. Preferably the acid is an organic acid, eg acetic acid. Preferably an excess of the amine is used. The reaction may be carried out in water or an organic solvent, for example, methanol, ethanol, isopropanol, propanol, acetonitrile, or dimethylsulphoxide. In the amine (II) preferably $R^1$ and $R^{2'}$ together represent a heterocyclic group as defined under (B) above or $R^1$ is hydrogen or lower alkyl and $R^2$ is hydrogen, lower alkyl or $-(CH_2)_n-R^3$ where n is as defined above and $R^3$ is aryl, $-OR^4$ or $-COOR^5$ (where $R^4$ and $R^5$ are as defined above). Where in the resulting compound the group $R^2$ is not the one required, the precursor group $R^2$ may be converted to the required group $R^2$ by methods known in the art for interconversion of such functional groups. Examples of such methods are given hereinbelow. An example of a protected form of the amine (III) is a cyclic amine such as that of formula

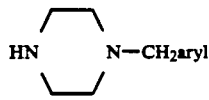

The protecting group, $-CH_2$aryl, may be removed after the Michael type reaction by means of catalytic hydrogenation.

An alternative method of preparing the compounds of the invention comprises reacting a compound of formula (II) as given above with a hydroxylamine derivative of formula $$R^{18}NHOR^{19} \qquad (IV)$$

where $R^{19}$ is hydrogen and $R^{18}$ is lower alkyl or $R^{19}$ is lower alkyl or aryl(lower)alkyl and $R^{18}$ is hydrogen or lower alkyl to give a compound of formula (V)

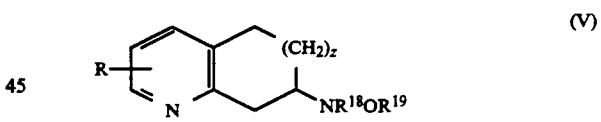

(where z, R, $R^{18}$ and $R^{19}$ are as given above), reducing the compound of formula (V) to give an amine of formula

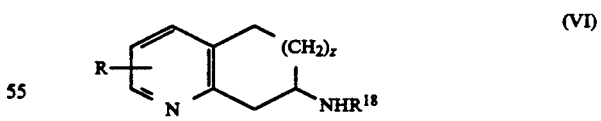

(where z and R have the meanings given above and $R^{18}$ is hydrogen or lower alkyl) and, if required, converting an amine of formula (VI) into another compound of formula (I) by methods known in the art.

The compounds of formula (V) are novel intermediates which are also provided by this invention.

The hydroxylamine of formula (IV), preferably as an acid addition salt, may be reacted with the compound of formula (II) preferably in an organic solvent.

The intermediate of formula (V) may be reduced to the amine of formula (VI) by, for example, catalytic hydrogenation or the use of a reducing agent such as aqueous titanium trichloride, or a dissolving metal reducing agent such as zinc/hydrochloric acid.

If in either of the above processes for preparing the compounds of the invention the group R on the compound (II) is affected by or interferes with the reaction the group may be replaced by another R group which may be converted to the desired R group at a later stage in the synthesis. For example, an amino group may be protected and the protecting group removed subsequently or the reaction may be carried on a nitro substituted starting material and the nitro group reduced to an amino group subsequently. Similarly a hydroxy group may be protected as an aryl(lower)alkyloxy group. Other interconversions are also possible, for example a reaction may be carried out with a halogen substituent which may subsequently be converted to a loweralkyloxy group.

Once a compound of general formula (I) is obtained it may be converted into another compound of formula (I) by interconversions of the —NR$^1$R$^2$ group by methods known in the art. Examples of such methods are given below:

1. An amino group may be acylated to an amide group by reacting with an acylating agent. The acylating agent may be, for example a carboxylic acid halide or anhydride or a carboxylic acid in presence of a condensing agent such as 1,1-carbonyldiimidazole.

Example so such interconversions are illustrated below.

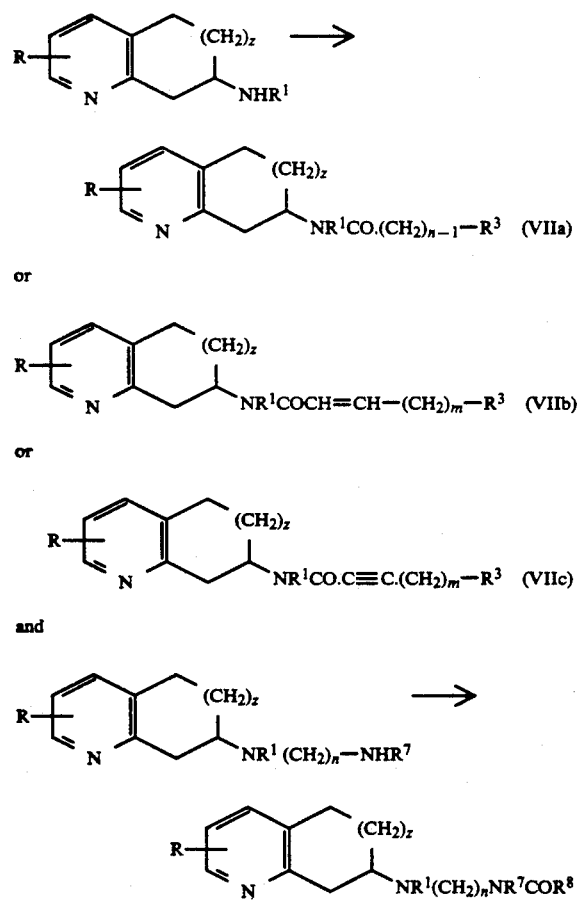

Compounds (VIIa), (VIIb) and (VIIc) are nvoel intermediates which are also provided by the present invention.

2. An amino group may be alkylated. When used in this connection "alkylated" is used to include the substitution of a primary amino group or a secondary amino group (a) as appropriate with one, or two substituted or unsubstituted alkyl groups. The substituent on the alkyl group can have any of the meanings of R$^3$ given above that do not interfere with the reaction.

The amino group may be alkylated by, for example, forming an amide group as indicated above and reducing the amide. The reduction can be carried out with a reducing agent such as an alkali metal borohydride or diborane. Another method of alkylation comprises condensation of the amino group with a reagent such as Z—(CH$_2$)$_n$—R$^3$ where n is as defined above, R$^3$ has any of the meanings given above that do not interefere with the reaction and Z is a leaving group, eg halogen or a sulphonyloxy group such as methylsulphonyloxy or 4-toluenesulphonyloxy. The condensation may be carried out in the presence of a base, eg caesium carbonate, diisopropylethylamine, triethylamine or potassium carbonate. A further method of akylation comprises reaction of the amine with an aldehyde and reduction of the resulting Schiff's base either in situ or after its isolation. The reduction may be carried out by catalytic hydrogenation or with a reducing agent such as an alkali metal cyanoborohydride or diborane. A compound in which —NR$^1$R$^2$ is —NH$_2$ may be alkylated to give a compound in which —NR$^1$R$^2$ is

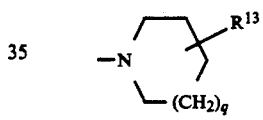

by reaction with an appropriate dihaloalkane.

3. A nitrile group may be reduced to an amine, eg with a metal hydride reducing agent or preferably catalytic hydrogenation.

4. A nitrile group may be hydrolysed to give an amide, acid or ester. An acid may be esterified to give an ester.

5. An alkoxycarbonyl group may be reduced, eg with a hydride reducing agent to an alcohol.

6. An amine may be converted to a sulphonamide or an aminosulphamoyl derivative by reaction with a sulphonyl halide or an amidosulphonyl halide. A cyclic sulphonamide may be prepared by intramolecular cyclisation of, for example an aminosulphonylalkylhalide.

7. Amines may be converted into urea derivatives by reaction with isocyanates or into carbamates by reaction with carbonic acid derivatives (eg a carbonate or carbonyl halide).

8. Alcohols may be converted into esters by the usual methods of esterification.

9. The compounds of formula (I) may be converted into their heteroaromatic N-oxides by methods known for preparing analogous compounds. For example the compounds may be oxidised with a peracid, hydrogen peroxide. an alkali metal peroxide or an alkyl peroxide If oxidation gives the di-oxide this may be subsequently reduced to give the desired mono N-oxide of the nitrogen containing heteroaromatic ring.

The processes described above may be carried out to give a compound of the invention in the form of a free base or as an acid addition salt. If the compound of the invention is obtained as an acid addition salt, the free base can be obtained by basifying a solution of the acid addition salt. Conversely, if the product of the process is a free base an acid addition salt, particularly a pharmaceutically acceptable acid addition salt, may be obtained by dissolving the free base in a suitable organic solvent and treating the solution with an acid, in accordance with conventional procedures for preparing acid edition salts from base compounds.

Examples of acid addition salts are those formed from inorganic and organic acids, such as sulphuric, hydrochloric, hydrobromic, phosphoric, tartaric, fumaric, maleic, citric, acetic, formic, methanesulphonic, p-toluenesulphonic, oxalic and succinic acids.

The compounds of the invention contain one or more asymmetric carbon atoms, so that the compounds can exist in different steroisomeric forms. The compounds can, for example, exist as racemates or optically active forms. The optically active forms can be obtained by resolution of the racemates or by asymmetric synthesis.

The starting materials of formula (II) are either described in the literature or may be prepared by methods known for analogous compounds. For example a 5,6,7,8-tetrahydroquinoline may be converted by known methods into a 8-hydroxy- or 8-arylthio- or 8-arylseleno-5,6,7,8-tetrahydroquinoline and this may be converted to the desired 5,6-dihydroquinoline of formula (II) in which z is 1. A 8-hydroxy compound may be dehydrated with, for example, polyphosphoric acid, while a 8-arylthio or 8-arylseleno compound may be oxidised by treatment with a peracid, such as 3-chloroperoxybenzoic acid, to form the sulphoxide or selenoxide which may then be subjected to a thermal elimination reaction to give the dihydroquinoline of formula (II). Similar processes can be used to prepare the starting materials in which z is 0 or 2.

The compounds of the present invention possess pharmacological activity. In particular, they act on the central nervous system by binding to 5-HT receptors. In pharmacological testing it has been shown that many of the compounds particularly bind to receptors of the 5-HT$_{1A}$ type. They exhibit activity as 5-HT$_{1A}$ agonists, antagonists or partial agonists and hence can be used for the treatment of CNS disorders, such as anxiety in mammals, particularly humans. They may also be useful as antihypertensives and in treating anorexia. Some compounds also posses $\alpha_2$-agonist activity making them particularly useful as antihypertensive agents. A particularly preferred antihypertensive agent is 7-azetidino-5,6,7,8-tetrahydroquinoline and the pharmaceutically acceptable salts thereof.

The compounds of the invention were tested for 5-HT$_{1A}$ receptor binding activity in rat hippocampal membrane homogenate by the method of B S Alexander and M D Wood, J Pharm Pharmacol, 1988, 40, 888–891. The results for representative compounds of the invention are given below.

| Compounds of Example | IC$_{50}$ (nM) |
| --- | --- |
| 3 | 137 |
| 12 | 138 |
| 15 | 42 |
| 16 | 26 |
| 19 | 9 |
| 20 | 68 |
| 35 | 131 |
| 38 | 55 |

| Compounds of Example | IC$_{50}$ (nM) |
| --- | --- |
| 50 | 136 |

The compounds are evaluated for 5-HT$_1$ receptor agonist activity in vivo by a method involving the assessment of 5-HT related behaviour in rats following i.v. administration of the test compound (M D Tricklebank et al, European Journal of Pharmacol, 1985, 106, 271–282). The ED$_{50}$ values (as calculated by the method of Kimball et al, Radiation Research, 1957, 7, 1–12) for the compounds of Examples 12, 16, 19, 38 and 50 were respectively 0.62, 0.81, 0.52, 0.57 and 1.10 mg/kg. Some of the compounds possess 5HT$_{1A}$ receptor antagonism activity; for example the compound of Example 16 possesses pA$_2$ of 7.7 in a test involving the antagonism of 8-hydroxy-2-(di-n-propylamino)tetralin in the guinea-pig ileum in vitro (Fozard et al, Br J Pharmac, 1985, 86, 601P).

The invention also provides a pharmaceutical composition comprising a compound of the invention in association with a pharmaceutically acceptable carrier. Any suitable carrier known in the art can be used to prepare the pharmaceutical composition. In such a composition, the carrier is generally a solid or liquid or a mixture of a solid and a liquid.

Solid form compositions include powders, granules, tablets, capsules (eg hard and soft gelatine capsules), suppositories and pessaries. A solid carrier can be, for example, one or more substances which may also act as flavouring agents, lubricants, solubilisers, suspending agents, fillers, glidants, compression aides, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, eg from 0.03 to 99%, preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups, elixirs and pressurised compositions. The active ingredient, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solibilizers, emulsifiers, buffers, preservatives, sweeteners, flavouring agents, suspending agents, thickening agents, colours, viscosity regulators, stabilisers or osmo-regulators. Suitable examples of liquid carriers for oral and parenteral administration include water (particularly containing additives as above eg cellulose derivatives, preferably sodium carboxymethyl cellulose solution), alcohols (including monohydric alcohols and polyhydric alcohols eg glycerol and glycols) and their derivatives, and oils (eg fractionated coconut oil and arachis oil). For parenteral administration the carrier can also be an oily ester such as ethyl oleate and ispropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. When the compound is orally active it can be administered orally either in liquid or solid composition form.

Preferably the pharmaceutical composition is in unit dosage form, eg as tablets or capsules. In such form, the composition is sub-divided in unit dose containing appropriate quantities of the active ingredient; the unit dosage forms can be packaged composition, for example packeted powders, vials, ampoules, prefilled syringes or sachets containing liquids. The unit dosage form can be, for example, a capsule or tablet itself, or it can be the appropriate number of any such compositions in package form. The quantity of the active ingredient in unit dose of composition may be varied or adjusted from 0.5 mg or less to 750 mg or more, according to the particular need and the activity of the active ingredient.

The following Examples illustrate the invention:

EXAMPLE 1

5,6,7,8-Tetrahydro-7-(N-hydroxymethylamino)quinoline

A solution of 5,6-dihydroquinoline (9.17g, 0.07 mmol) in methanol (10 ml) at 0° was treated portionwise with N-methylhydroxylamine hydrochloride (11.5 g, 0.138 mmol), stirred for 2 h, poured into saturated aqueous sodium bicarbonate (250 ml), and extracted with chloroform (3×150 ml). The extracts were washed with water (50 ml), dried (MgSO$_4$), and evaporated in vacuo. The residual brown liquid was purified by chromatography (alumina; ether) to give the product (6.45 g) as a colourless oil, which was converted into the amine of Example 2.

EXAMPLE 2

5,6,7,8-Tetrahydro-7-(methylamino)quinoline

A stirred solution of 20% aqueous titanium trichloride (35 ml, 45 mmol) at 0° was treated dropwise with a solution of the hydroxylamine of Example 1 (5.2 g, 29.9 mmol) in methanol (120 ml), warmed to room temperature and after 2 h evaporated in vacuo. The viscous oil at 0° was treated cautiously with 20% aqueous potassium hydroxide (100 ml) with stirring, filtered, and the solid washed with water (2×50 ml) and dichloromethane (2×100 ml). The layers of the fitrate were separated and the aqueous phase extracted with dichloromethane (2×200 ml). The combined organic phases were dried (Na$_2$SO$_4$) and evaporated in vacuo. The brown oil was purified by short-path distillation to give the free base (3.90 g, 81%) as a colourless oil, bp 125°-130° (bath temp.)/0.15 mm Hg. A solution of the oil (0.6 g) in methanol (5 ml) was acidified with ethereal hydrogen chloride and evaporated in vacuo. The gum in hot propan-2-ol (5 ml) was treated dropwise with methanol until solution occurred. The solution was concentrated to half-volume and cooled to room temperature. The precipate was filtered and washed with propan-2-ol to give the product as the dihydrochloride hemihydrate (0.80 g), mp 162°-163°. (Found: C, 49.1; H, 6.7; N, 11.35.

$C_{10}H_{14}N_2.HCl.\frac{1}{2}H_2O$ requires C, 49.2; H, 7.0; N, 11.5%).

EXAMPLE 3

5,6,7,8-Tetrahydro-7-dimethylaminoquinoline

Sodium cyanoborohydride (1.0 g, 16 mmol) was added portionwise to a stirred solution of the product of Example 2 (1.61 g, 10 mmol) and 40% w/v aqueous formaldehyde (3.8 ml, 50 mmol) in acetonitrile (30 ml) at 0°. After 15 min the acidity of the solution was adjusted to ca pH. 7 by the dropwise addition of acetic acid, and this pH was maintained for 45 min by further judicious additions of acetic acid. The solution was evaporated in vacuo, the residue treated with 2N-KOH (40 ml), and the mixture extracted with ether (3×50 ml). The extracts were washed with 0.5N-KOH (20 ml) and extracted with 1N-HCl (3×20 ml). The acidic extracts were combined, basified with sodium carbonate. and extracted with ether (3×50 ml). The extracts were dried (MgSO$_4$) and evaporated in vacuo to leave the free base as a pale yellow oil. Treatment of the oil with methanolic hydrogen chloride and evaporation of the solvent in vacuo gave a hygroscopic solid which was crystallised from methanol-propan-2-ol to give the as the dihydrochloride (0.81 g) mp 158°-160°.

(Found: C, 53.0; H, 6.5; N, 11.6. $C_{11}N_{16}N_2.2HCl$ requires C, 53.0; H, 6.5; N, 11.2%).

EXAMPLE 4

5,6,7,8-Tetrahydro-7-(N-methyl-N-propylamino)quinoline

A mixture of the amine of Example 2 (1.62 g, 10 mmol), propanal (5.8 g, 100 mmol) and 5% palladium-charcoal (0.16 g) in ethanol (20 ml) was stirred vigorously under an atmosphere of hydrogen at S.T.P. until hydrogen uptake ceased. The mixture was filtered and the filtrate evaporated in vacuo to leave an oil which was partitioned between 2N-HCl (25 ml) and ethyl acetate (50 ml). The organic layer was separated and extracted with water (25 ml). The combined aqueous extracts were washed with ethyl acetate (2×50 ml), basified with saturated aqueous sodium bicarbonate, and extracted with chloroform (3×50 ml). The chlorinated extracts were dried (Na$_2$SO$_4$) and evaporated in vacuo to leave an oil which was chromatographed (alumina; ether) to give the free base (0.8 g) as an oil. A solution of the oil in methanol (5 ml) was acidified with ethereal hydrogen chloride and evaporated in vacuo. The orange gum was crystallised by trituration with hot tetrahydrofuran (10 ml) and propan-2-ol (5 ml) to give the product as the dihydrochloride (0.9 g) mp 158°-159°.

(Found: C, 56.1; H, 8.14; N, 10.0. $C_{13}H_{20}N_2.2HCl$ requires C, 56.3; H, 8.00; N, 10.1%).

EXAMPLE 5

5,6,7,8-Tetrahydro-7-(N-methyl-N-butylamino)quinoline

A mixture of the amine of Example 2 (1.62 g, 10 mmol), butanal (7.21 g, 100 mmol), and 5% palladium-charcoal (0.16 g) in ethanol (20 ml) was stirred under H$_2$ at S.T.P. until gas uptake ceased. The mixture was filtered and the filtrate evaporated in vacuo to give a viscous oil which was partitioned between ethyl acetate (50 ml) and 2N-HCl (25 ml). The organic layer was separated and extracted with 2N-HCl (25 ml). The combined aqueous phases were washed with ethyl acetate (3×50 ml), basified with 2N-NaOH, and extracted with chloroform (2×50 ml). The extracts were dried (MgSO$_4$) and evaporated in vacuo to give the free base as an oil. A solution of the oil in methanol (10 ml) was acidified with ethereal hydrogen chloride and evaporated in vacuo. The gum was dissolved in a mixture of hot tetrahydrofuran (25 ml) to which the minimum quantity of propan-2-ol (ca. 10 ml) had been added. Cooling to room temperature induced the crystallisation of the product as the dihydrochloride quarter hydrate (2.31 g) mp 132.5°–133.5°.

(Found: C, 57.1; H, 8.15; N, 9.2. $C_{14}H_{22}N_2 \cdot 2HCl \cdot \frac{1}{4}H_2O$ requires C, 57.2; H, 8.4; N, 9.5%).

EXAMPLE 6

N-[7-(5,6,7,8-Tetrahydroquinolinyl)]-N-methyl-2,2-dimethylpropanamide

A stirred solution of trimethylacetyl chloride 2.41 g, 20 mmol) in chloroform (25 ml) at 0° was treated dropwise with a solution containing the amine of Example 2 (1.62 g, 10 mmol) and triethylamine (4.2 ml, 30 mmol) in chloroform (25 ml), after 2 h washed with water (2×50 ml) and saturated aqueous sodium bicarbonate (50 ml), dried (Na$_2$CO$_3$), and evaporated in vacuo to give a solid. Recrystallisation from hexane gave the product (2.20 g) mp 112°–114°.

(Found: C, 73.0; H, 9.1; N. 11.2. $C_{15}H_{22}N_2O$ requires C, 73.1; H, 9.0; N, 11.4%).

EXAMPLE 7

5,6,7,8-Tetrahydro-7-[N-methyl-N-2,2-dimethylpropyl)amino]quinoline

A solution of the product of Example 6 (1.8 g, 7.5 mmol) in tetrahydrofuran (40 ml) at 0° was treated with 1.0 M borane-tetrahydrofuran complex in tetrahydrofuran (75 ml) under an atmosphere of nitrogen, after 2 h treated cautiously with 10 N-HCl (50 ml), stirred for 18h, and evaporated in vacuo. The syrup was dissolved in water (50 ml) and the solution washed with ethyl acetate (3×50 ml), basified with 10N-NaOH, and extraced with chloroform (3×50 ml). The extracts were dried (Na$_2$SO$_4$) and evaporated in vacuo to give an oil which was purified by short column chromatography (alumina; chloroform) to give the free base as a colourless liquid. The base was dissolved in methanol (5 ml) and the solution acidified with ethereal hydrogen chloride. Evaporation in vacuo gave a yellow amorphous solid which was crystallised from ethyl acetate-propan-2-ol (20:13) to give the product as the dihydrochloride hydrate (1.67 g), sublimes 210° –220°.

Found: C, 56.05; H, 8.5; N, 8.8. $C_{15}H_{24}N_2 \cdot 2HCl \cdot H_2O$ requries C, 55.7; H, 8.7; N, 9.7%).

EXAMPLE 8

N-[7-(5,6,7,8-Tetrahydroquinolinyl)]-N-methylphenylacetamide

This compound was prepared from the amine of Example 2 (1.3 g, 8.0 mmol), triethylamine (3.4 ml, 24.0 mmol), and phenylacetyl chloride (2.1 ml, 16.0 mmol) using the method described in Example 6. The crude gum was purified by chromatography (aluminia; ether) to give the product (1.55 g) as an oil which was converted into the amine of Exmaple 9.

EXAMPLE 9

5,6,7,8-Tetrahydro-7-[N-methyl-N-(phenylethyl)amino]quinoline

This compound was prepared from the amide of Example 8 (1.4 g, 5.0 mmol), and 1.0 M borane-tetrahydrofuran compelx in tetrahydrofuran (50 ml, 50 mmol) using the method described in Example 7. The crude free base was isolated as a yellow liquid which was purified no further but converted directly into the product as the dihydrochloride one and one quarter hydrate (0.52 g), mp 146°–147°.

(Found: C, 59.5; H, 7.2; N, 8.1. $C_{18}H_{22}N_2 \cdot 2HCl \cdot 1\frac{1}{4}H_2O$ requires C, 59.75; H, 7.4; N, 7.7%).

EXAMPLE 10

5,6,7,8-Tetrahydro-7-(N-hydroxy-1-propylamino)quinoline

A mixture of 5,6-dihydroquinoline (9.5 g, 72.5 mmol) and 1-propylhydroxylamine hydrochloride (7.96 g, 72.5 mmol) was stirred with ice-bath cooling for 1 h. The thick syrup was dissolved in chloroform (200 ml) and washed with saturated aqueous sodium bicarbonate (2×100 ml). The aqueous layer was separated and washed with chloroform (2×100 ml). The chlorinated extracts were dried (MgSO$_4$) and evaporated in vacuo to give yellow crystals (5.2 g) of the free base, mp 82.5°–84.0° (from cyclohexane), together with a brown oil (12.0 g). The oil was chromatographed (alumina; chloroform) to give a second crop of the free base (3.7 g overall yield). The crystals were dissolved in propan-2-ol (5 ml) and the solution acidified with ethereal hydrogen chloride. Scratching induced crystallisation of the product, as the dihydrochloride, mp 120°–122.5°.

(Found: C, 51.6; H, 7.3; N, 9.85; $C_{12}H_{18}N_2O \cdot 2HCl$ requires C, 51.6; H, 7.2; N, 10.0%).

EXAMPLE 11

5,6,7,8-Tetrahydro-7-(1-propylamino)quinoline

A stirred solution of titanium trichloride, 15 wt. % solution in 20–30 wt. % hydrochloric acid (31.5 ml, 30 mmol) was treated dropwise with the product of Example 10 (3.1 g, 15 mmol) in MeOH, 30 mmol), after 15 min evaporated in vacuo, and the residual solid treated with 5N-NaOH (60 ml) and extracted with ether (4×100 ml). The extracts were dired (MgSO$_4$) and evaporated in vacuo to give a brown oil. Purification by short path distillation gave the free base (1.9 g, 67%) as a pale yellow oil, bp 114°–120° (bath temp)/0.03 mm Hg. A soluiton of the oil in propan-2-ol (5 ml) was acidified with etheral hydrogen chloride. The precipitate was filtered, washed with a small quantity (0.5 ml) of propan-2-ol, and dried in vacuo to give the product, as the dihydrochloride hydrate, mp 156°–159°.

(Found: C, 51.3; H, 8.1; N, 9.7. $C_{12}H_{18}N_2 \cdot 2HCl \cdot H_2O$ requires C, 51.25; H, 7.9; N, 10.0%).

EXAMPLE 12

5,6,7,8-Tetrahydro-7-(1,1-dipropylamino)quinoline

This compound was prepared by two methods.

(a) Propionic acid (7.5 ml, 102 mmol) was added dropwise to a stirred suspension of sodium borohydride (1.15 g, 30 mmol) in dry benzene (125 ml). After 6 h a solution of the product of Example 11 (0.95 g, 5. 0 mmol) in dry benzene (10 ml) was added dropwise and the solution heated under reflux for 4 h, cooled, and the mixture stirred with 2N-NaOH (250 ml) for 2 h. The mixture was extracted with ether (3×100 ml) and the extracts were dried (MgSO$_4$) and evaporated in vacuo. The residue was dissolved in 2N-HCl and the solution heated to 75°, cooled, washed with ether (50 ml), basified with concentrated aqueous ammonia, and extracted with dichloromethane (2×50 ml). The extracts were dired (MgSO$_4$) and evaporated in vacuo to leave an oil (1.0 g) which was chromatographed (alumina; dichloromethane) to give the free base (0.44 g) as a colourless oil. A solution of the oil in propan-2-ol (5 ml) was acidified with ethereal hydrogen chloride and evaporated in vacuo.

A mixture of the residue in hot tetrahydrofuran (10 ml) was treated dropwise with propan-2-ol until a clear solution was formed. Cooling to room temperature and scratching induced crystallisation of the product as the dihydrochloride three-quarter hydrate, mp>200° (dec.)

(Found: C, 56.4; H, 8.6; N, 9.2. $C_{15}H_{24}N_2.2HCl.\frac{3}{4}H_2O$ requires C, 56.5; H, 8.7; N, 8.8%).

(b) a mixture of the product of Example 11 (5.2 g, 27.4 mmol), propanal (16.3 g, 280 mmol), and 5% palladium-charcoal (0.53 g) in ethanol (50 ml) was stirred under an atmosphere of hydrogen at S.T.P. until the uptake of gas cceased. The catalyst was removed by filtration and the filtrate evaporated in vacuo. The residual oil was partitioned between 2N-HCl (50 ml) and ethyl acetate (100 ml). The layers were separated and the organic phase extracted with 2N-HCl (30 ml). The aqueous phases were combined, washed with ethyl acetate (3×100 ml), basified with 2N-NaOH, and extraced with chloroform (3×100 ml). The chlorinated extracts were dired (Na$_2$SO$_4$) and evaporated in vacuo to give an oil. Chromatography [alumina; hexane-ether (1:1)] gave the free base (4.02 g) as an oil. Conversion to the dihydrochloride salt was performed as described under Example 12(a).

EXAMPLE 13

2,3-Dihydro-N-[7-(5, 6, 7, 8-tetrahydroquinolinyl)]-N-propyl-1,4-benzodioxin-2-carboxamide This compound was prepared from the amine of Example 11 (1.90 g, 10.0 mmol), triethylamine (2.77 ml, 20.0 mmol) and 2,3-dihydro-1,4-benzodioxin-2-carbonyl chloride (1.88 g, 9.5 mmol) using the method described in Example 6. The crude gum was purified by chromatography (silica; ether) to give the product (2.30 g, 69%) as an oil which was converted into the thioamide of Example 14.

EXAMPLE 14

2,3-Dihydro-N-[7-(5,6,7,8-tetrahydroquinolinyl)]-N-propyl-1,4-benzodioxin-2-carbothioamide A mixture of the amide of Example 13 (2.0 g, 5.7 mmol) and Lawesson's reagent (2.41 g, 5.9 mmol) in dry dioxan (20 ml) was heated at 80° for 16 h, cooled to room temperature, filtered through a short column of alumina, and evaporated in vacuo to give a yellow foam. Crystallisation was induced by trituration with ether to give the product (1.84 g) as a pale yellow solid which was converted into the amine of Example 15.

EXAMPLE 15

5,6,7,8-Tetrahydro-7-{-N-[2-(2,3-dihydro-1,4-benzodioxinyl]methyl-N-propyl}aminoquinoline A solution of the thioamide of Example 14 (1.84 g, 5.0 mmol) in dioxan (30 ml) was treated under an atmosphere of nitrogen with Raney nickel (1 spatula spoonful), heated at 55° for 1 h, cooled to room temperature, and filtered. The solution was thrice more treated with Raney nickel (1 spatula spoonful) and each time stirred at room temperature for 24 h. Evaporaiton in vacuo gave a yellow gum which was chromatographed [silica; hexane-ethyl acetate (1:1] to give the free base as an oil. A solution fo the base in methanol (5 ml) was acidified with ethereal hydrogen chloride and evaporated in vacuo. The pale yellow foam was crystallised from tetrahydrofuran-propan-2-ol (5:2) to give the product as the dihydrochloride quarter hydrate (0.25 g) mp 123°–125°.

(Found: C, 60.6; H, 7.1; N, 7.0. $C_{21}H_{26}N_2O_2.HCl.\frac{1}{4}H_2O$ requires C, 60.65; H, 6.9; N, 6.7%).

EXAMPLE 16

8-{4-[N-(5,6,7,8-Tetrahydroquino]in-7-yl)-N-methyl]aminobutyl}-8-azaspiro[4.5]decan-7,9-dione A stirred mixture of the product of Example 2 (1.62 g, 10.0 mmol), 8-methylsulphonyloxybutyl]-8-azaspiro[4.5]decan-7,9-dione (3.17 g, 10.0 mmol), and caesium carbonate 3.26 g, 10.0 mmol) in dimethylformamide (15 ml) was heated under an atmosphere of nitrogen at 100° for 4 h, cooled to room temeprature, treated with water (50 ml), and extracted with ether (3×50 ml). The extracts were washed with water (50 ml), dried (Na$_2$SO$_4$), and evaporated in vacuo to give a brown oil which was purified by chromatography [alumina; hexane-ethyl acetate (1:1)]. The free base was dissolved in propan-2-ol and the solution acidified with ethereal hydrogen chloride. Evaporation in vacuo gave an amorphous solid which was crystallised from tetrahydrofuran-propan-2-ol (5:1). Recrystallisation from propan-2-ol gave the product as the dihydrochloride hydrate (1.39 g) mp (136°–138°.

(Found: C, 58.5; H, 7.9; N, 8.6. $C_{23}H_{33}N_2O.2HCl.H_2O$ requires C, 58.2; H, 7.9; N, 8.9%).

EXAMPLE 17

N-[7-(5,6,7,8-Tetrahydroquinolinyl)]-N-propylaminoacetonitrile

A solution of the product of Example 11 (2.85 g, 15 mmol), chloroacetonitrile (1.13 g, 15 mmol), and diisopropylethylamine (2.6 ml, 15 mmol) in dimethylformamide (30 ml) was heated at 100° for 1 h, poured into water (200 ml) and extracted with ether (3×100 ml). The extracts were washed with water (100 ml), dried (Na$_2$SO$_4$), and evaporated in vacuo to give a red oil. Purification by chromatography [silica; hexane-ethyl acetate (1:1)] gave the product (1.20 g) as an orange oil which was converted into the amine of Example 18.

EXAMPLE 18

7-{N-[2-(Aminoethyl)]-N-propyl]amino-5,6,7,8-tetrahydroquinoline

A mixture of the product of Example 17 (1.20 g, 5.25 mmol) and Raney nickel (1 spatula spoonful) in 50% saturated ethanolic ammonia (100 ml) was shaken under hydrogen at 55 psi for 18 h. More Raney nickel (1 spatula spoonful) was added and the mixture shaken under hydrogen at 55 psi for a further 21 h. The mixutre was filtered and the filtrate evaporated in vacuo to give the crude product as a pale brown oil (1.18 g) which was converted without purification into the amide of Example 19.

EXAMPLE 19

4-Fluoro-N-{2-[N'-(5,6,7,8-tetrahydroquinolin-7-yl)-N'-propyl]aminoethyl]}benzamide A stirred solution of the product of Example 18 (1.17 g, 4.5 mmol) and triethylamine (1.38 ml, 9.9 mmol) in dichloromethane (10 ml) was treated with a solution of 4-fluorobenzoyl chloride (0.75 g, 4.7 mmol) in dich-)oromethane (10 ml). After 0.5 h the solvent was evaporated in vacuo and the residue partitioned between saturated aqueous sodium bicarbonate and dichloromethane. The layers were separated and the aqueous layer extracted with dichloromethane (10 ml). The combined organic phases were dried ($Na_2SO_4$), evaporated in vacuo, and the residue was purified by chromatography [alumina; hexane-ethyl acetate (1:1)] to give the free base as a gum. A solution of the gum in methanol was acidified with ethereal hydrogen chloride, evaporated in vacuo, and the solid dried at 40° in vacuo to give the product as the dihydrochloride one and a half hydrate (0.36 g) as hygroscopic crystals, mp 131°–135°.

(Found: C, 55.9; H, 6.6; N, 9.1. $C_{21}H_{26}FN_3O.2HCl1.5H_2O$ requires C, 56.0; H, 6.9; N, 9.3%).

EXAMPLE 20

7-Amino-5,6,7,8-tetrahydro-N-{2-[2-(2,3-dihydro-1,4-benzodioxinyl)]ethyl}-N-methylquinoline A mixture of the product of Example 2 (0.8 g, 5.0 mmol), 2-(2-chloroethyl)-2,3-dihydro-1,4-benzodioxin (1.2 g, 6.0 mmol), potassium iodide (0.25 g, 1.5 mmol) and triethylamine (0.5 g, 5.0 mmol) in dimethylformamide (10 ml) was heated at 75° for 9 h, cooled to room temperature, diluted with water (50 ml), basified with saturated aqueous sodium carbonate, and extracted into ether (3×50 ml). The extracts were washed with 1M-HCl (3×10 ml). The acid washings were washed with dichloromethane (10 ml), basified with 33% aqueous ammonia, and extracted with dichloromethane (3×50 ml). The chlorinated extracts were dried ($MgSO_4$) and evaporated in vacuo to give the free base as an oil. The oil was dissolved in ethanol (6 ml) and the solution acidified with a solution of hydrobromic acid in ethanol-ethyl acetate (1:1). On standing a precipitate formed which was filtered and washed with ethanol (1 ml) and ether (3×10 ml) to give the product as the dihydrobromide hydrate (0.55 g), mp 158°–160°.

(Found: C, 47.4; H, 5.5; N, 5.5. $C_{20}H_{24}N_2O_2.2HBr.H_2O$ requires C, 47.6; H, 5.6; N, 5.55%).

EXAMPLE 21

5,6,7,8-Tetrahydro-N-methyl-N-[3-(2,6-dimethoxyphenoxy)propyl]-7-aminoquinoline A solution of the product of Example 2 (0.81 g, 5.0 mmol) in dry dimethyiformamide (10 ml) was treated with diisopropylethylamine (0.65 g, 5.0 mmol), treated with 3-(2,6-dimethoxyphenoxy)propyl bromide (1.3 g, 5.0 mmol), stirred for 48 hours and evaporated in vacuo to give a red oil, which was partitioned between ether (50 ml) and saturated aqueous sodium carbonate (50 ml). The aqueous phase was extracted with ether (50 ml). The combined ether layers were extracted with 2N-HCl (2×50 ml) and the acidic extracts basified with potassium hydroxide and extracted with ch)oroform (2×30 ml). The chlorinated extracts were washed with water (50 ml), dried ($MgSO_4$), and evaporated in vacuo to give the free base as an oil. A solution of the oil in ethano was treated with hydrobromic acid in ethylacetate. The product, as the dihydrobromide hydrate, crystallised after 7 days as cream crystals (1.10 g), mp 103°–109°.

(Found: C, 46.6; H, 5.9; N, 5.3. $C_{21}H_{28}N_2O_3.2HBr.H_2O$ requires C, 47.0; H, 6.0; N, 5.2%).

EXAMPLE 22

2,6-Difluoro-N-[7-(5,6,7,8-tetrahydroquinolinyl)]-N-methylphenylacetamide 1,1'-Carbonyldiimidazole (3.24 g, 20.0 mmol) was added to a stirred solution of 2,6-difluorophenylacetic acid (3.44 g, 20.0 mmol) in dry acetonitrile (45 ml). After 30 min, a solution of the product of Example 2 (3.24 g, 20.0 mmol) in dry acetonitrile (30 ml) was added dropwise. The solution was stirred for 15 h and evaporated in vacuo. The pale yellow solid was dissolved in ethyl acetate (90 ml) and the solution extracted with 1N-HCl (2×100 ml). The extracts were washed with ethyl acetate (50 ml), basified with 10N-NaOH (50 ml), and extracted with ethyl acetate (3×100 ml). The organic extracts were washed with water (3×100 ml), dried ($Na_2SO_4$), and evaporated in vacuo to give a solid. Recrystallisation from acetonitrile gave the product (4.64 g), mp 155°–156°.

(Found: C, 68.4; H, 5.85; N, 8.75. $C_{18}H_{18}F_2N_2O$ requires C, 68.35; H, 5.75; N, 8.85%).

EXAMPLE 23

7-{N-[2-(2,6-Difluoropheny])ethyl]-N-methylamino}-5,6,7,8-tetrahydroquinoline Borane-methylsulphide complex (4.2 ml, ca. 42 mmol) was added dropwise to a stirred solution of the product of Example 22 (4.43 g, 14.0 mmol) in dry tetrahydrofuran (42 ml) at 70° under an atmosphere of nitrogen. The reaction mixture was heated under refiux for 24 h, cooled to −10°, and quenched by the dropwise addition of methanol (10 ml). Evaporation in vacuo gave a white foam which was treated with 5N-HCl (100 ml). The mixture was heated at 130° for 30 minutes, cooled to room temperature, and evaporated in vacuo. The gum was treated with water (50 ml) and the solution basified with 10N-NaOH (10 ml), extracted with chloroform (3×50 ml), and the extracts dried ($Na_2SO_4$) and evaporated in vacuo. The yellow oil was purified by chromatography (alumina; ether) to give the free base as an oil. The oil was dissolved in ethyl acetate (180 ml) and the solution acidified with ethereal hydrogen chloride (10 ml). The precipitate was filtered and dried in vacuo to give the product as the dihydrochloride one and a half hydrate (4.42 g), mp 172–°178°.

(Found: 53.75; H, 6.6, N, 6.6. $C_{18}H_{20}F_2N_2.2HCl.$ 1½$H_2O$ requires C, 53.75; H, 6.25; N, 6.95%).

EXAMPLE 24

5,6,7,8-Tetrahydro-4-methyl-7-(N,N-dipropylamino)quinoline

Step 1: 5,6,7,8-tetrahydro-4-methylquinoline-N-oxide

A stirred suspension of 3-chloroperoxybenzoic acid (34 g, 197 mmol) in dichloromethane (170 ml) at 0° was treated dropwise with 5,6,7,8-tetrahydro-4-methylquinoline (23.7 g, 161 mmol) in dichloromethane (30 ml), warmed to room temperature, washed with 1N-NaOH (3×200 ml), and extracted with dichloromethane (5×150 ml). The extracts were dried ($MgSO_4$) and evaporated in vacuo to give the product (21 g) as an oil.

Step 2: 5,6,7,8-tetrahydro-8-hydroxy-4-methylquinoline

A solution of the crude product of Step 1 (19.2 g, 115 mmol) in acetic anhydride (100 ml) was heated at 110° for 1 h, cooled to room temperature, and evaporated in vacuo. The residue was dissolved in methanol (100 ml) and the solution treated with 4N-NaOH (100 ml). After 2 h, the solution was concentrated in vacuo and the aqueous residue partitioned between dichloromethane (100 ml) and water (100 ml). The chlorinated phase was dried ($Na_2SO_4$), and evaporated in vacuo to give an oil which was purified by chromatography (silica; ether) to give the product as crystals (12.0 g).

Step 3 : 8-(5,6,7,8-tetrahydro-4-methylquinolinyl) methanesulphonate

A solution of the product of Step 2 (7.6g, 46 mmol) in dichloromethane (125 ml) at 0° was treated with triethylamine (7.0 ml, 50 mmol), treated with methanesulphonyl chloride 94.0 ml, 52 mmol), stirred for 30 min, washed with 0.1N-NaOH (2×200 ml), dried ($MgSO_4$), and evaporated in vacuo. The residue was purified by chromatography (silica; ether) to give the product (9.5 g) as an oil.

Step 4: 5,6,7,8-tetrahydro-4-methyl-8-(phenylthio)-quinoline

A suspension of sodium hydride [obtained from 80% dispersion in oil (1.5 g, 50 mmol)] in dimethylformamide (80 ml) was treated with thiophenol (0.6 ml, 5.8 mmol), stirred for 25 min, treated with a solution of the product of Step 3 (9.5 g, 39.4 mmol) in dimethylformamide (100 ml), stirred for 30 min, treated with 0.1N-NaOH (500 ml), and extracted with ether (3×500 ml). The extracts were washed with saturated aqueous sodium chloride (500 ml), dried ($Na_2SO_4$), and evaporated in vacuo to give the crude product (10.0 g) as an oil.

Step 5: 5,6,7,8-tetrahydro-4-methyl-8-(phenylsulphinyl)quinoline.

A solution of the product of Step 4 (10.0 g, 39.2 mmol) in dichloromethane (200 ml) was treated portionwise with 86% 3-chloroperoxybenzoic acid (8.0 g, 40 mmol) at <10°, stirred for 30 min, washed with 0.1N-NaOH, dried ($Na_2SO_4$) and evaporated in vacuo to give the crude product (10.8 g) as a solid.

Step 6: 5,6-dihydro-4-methylquinoline

The crude product of Step 5 (10.8 g, 40.0 mmol) was heated under reflux in toluene (100 m) for 30 min, cooled to room temperature, and extracted with 1N-HCl (3×50 ml). The extracts were basified with 10N-NaOH and extracted with dichloromethane (3×200 ml). The organic extracts were dried ($MgSO_4$) and evaporated in vacuo to give an oil which was purified by chromatography (alumina; ether) to give the product (5.5 g, 95%) as an oil.

Step 7: 5,6,7,8-tetrahydro-7-(N-hydroxy-1-propylamino)-4-methylquinoline

This compound was prepared from the product of Step 6 (4.5 g, 30 mmol), 1-propylhydroxylamine hydrochloride (6 g, 55 mmol), and methanol (20 ml) by the method outlined in Example 10. The crude material was recrystallised from cyclohexane to give the product (4.85 g).

Step 8: 5,6,7,8-tetrahydro-4-methyl-7-(1-propylamino)quinoline

This compound was prepared from the product of Step 7 (4.4 g, 20 mmol), titanium trichoride, 20 wt. % solution in 20–30 wt. % hydrochloric acid (23 ml, 30 mmol), and methanol (50 ml) using the procedure described in Example 11. The crude product (4.2 g, 81%) was converted into the product of Step 9 without purification.

Step 9: N-[7-(5,6,7,8-tetrahydro-4-methyl-quinolinyl)]-N-propylpropionamide

A solution of the crude product of Step 8 (4.2 g, 20.6 mmol) and triethylamine (3.5 ml, 35.2 mmol) in dichloromethane (100 ml) was treated with propionic anhydride (2.7 ml, 21.1 mmol), stirred for 30 min, washed with 0.1N-NaOH (100 ml), dried ($MgSO_4$), and evaporated in vacuo to give the crude product (5.0 g) as an oil.

Step 10: 5,6,7,8-tetrahydro-4-methyl-7-(N,N-dipropylamino)quinoline dihydrochloride A solution of the crude amide from Step 9 (50 g, 19.2 mmol) in dry tetrahydrofuran (50 ml) was treated under an atmosphere of nitrogen with borane-tetrahydrofuran complex, 1.0M solution in tetrahydrofuran (90 ml), stirred for 16 h, treated with 0.1N-HCl (100 ml), and concentrated in vacuo. The aqueous residue was partitioned between 0.1 N-NaOH (100 ml) and dichloromethane (100 ml). The organic phase was dried ($Na_2SO_4$), evaporated in vacuo, and the residue purified by chromatography (alumina; ether) to give the free base as an oil. A solution of the base in methanol 10 ml) was acidified with ethereal hydrogen chloride, evaporated in vacuo, and the residue crystallised from tetrahydrofuran-propan-2-ol (5:1) to give the product as the dihydrochloride (2.4 g), as hygroscopic crystals, mp 190°–192°.

(Found: C, 60.0; H, 9.0; N, 8.5. $C_{16}H_{26}N_2$. 2HCl requires C, 60.2; H, 8.8; N, 8.8%).

EXAMPLE 25

5,6,7,8-Tetrahydro-3-methyl-7-(N,N-dipropylamino)quinoline

Step 1: 5,6,7,8-tetrahydro-3-methyl-8-(phenylseleno)-quinoline

A solution of 5,6,7,8-tetrahydro-3-methylquinoline (7.5 g, 51 mmol) in tetrahydrofuran (100 ml) was treated under an atmosphere of nitrogen with 1.5%-butyllithium in hexane (35 ml, 52 mmol) at 0°. The resulting red solution was added to a solution of phenylselenyl chloride (10 g, 52 mmol) in tetrahydrofuran (50 ml) at 0°. After 30 min, water (100 ml) was added and the mixture concentrated in vacuo. The aqueous residue was partitioned between saturated aqueous sodium chloride (100 ml) and ether (100 ml). The organic phase was dried (Na$_2$SO$_4$) and evaporated in vacuo to give the crude product (15.2 g) as an oil.

Step 2: 5,6-dihydro-3-methylquinoline

A solution of the crude product of Step 1 (4.2 g, 13.9 mmol) in dichloromethane (100 ml) at −40° was treated portionwise with 86% 3-chloroperoxybenzoic acid (3.0 g, 14.9 mmol). After 30 min, the mixture was warmed to room temperature, washed with 2N-NaOH (2×100 ml), dried (MgSO$_4$), and evaporated in vacuo. The residue was dissolved in 1N-H$_2$SO$_4$ (100 ml) and the solution washed with ether (3×100 ml), basified with sodium carbonate, and extracted with dichoromethane (3×100 ml). The chlorinated extracts were dried (MgSO$_4$) and evaporated in vacuo. The residue was distilled to give the product (1.79 g) as an oil.

Step 3: 5,6,7,8-tetrahydro-7-(N-hydroxy-1-propylamino)-3-methylquinoline.

This compound was prepared from the product of Step 2 (5.7 g, 39 mmol), 1-propylhydroxy)amine hydrochloride (5 g, 45 mmol), and methanol (50 m) by the method described in Example 10. The crude material was purified by chromatography [silica; ether-triethylamine (100:1)] to give the product (4.45 g) as an oil.

Step 4: 5,6,7,8-tetrahydro-3-methyl-7-(1-propylamino)quinoline

This compound was prepared from the product of Step 3 (4.45 g, 20 mmol), titanium trichloride, 20 wt. % solution in 20 wt. % hydrochloric acid (23 ml, 30 mmol), and methanol (50 ml) using the procedure described in Example 11. The crude amine (4.0 g) was converted directly into the product of Step 5.

Step 5: N-[7-(5,6,7,8-tetrahydro-3-methylquinolinyl)]-N-propylpropionamide

This compound was prepared from the crude product of Step 4 (4.0 g, 19.6 mmol), triethylamine (3.5 ml, 25.2 mmol), propionic anhydride (2.7 ml, 21.1 mmol), and dichloromethane (100 ml) using the way outlined in Example 24, Step 9. The crude amide (5.0 g) was converted into the amine of Step 6 without purification.

Step 6: 5,6,7,8-tetrahydro-3-methyl-7-(N,N-dipropylamino)quinoline dihydrobromide This compound was prepared form the crude amide of Step 5 (5.0 g, 19.2 mmol), borane-tetrahydrofuran complex, 1M solution in tetrahydrofuran (50 ml), and tetrahydrofuran (50 ml) using the method outlined in Example 24, Step 10, with the exception that the decomposition of the boron-product complex required stirring in 10N-HCl (50 m) for 18h. The free base was isolated by chromatography [alumina; hexane-ether (2:1)], dissolved in hot propan-2-ol (10 ml), and the solution acidified with 48% hydrobromic acid. The solution was evaporated in vacuo to give the product as the dihydrobromide (3.73 g) mp 197°-200° (from methanol-ethyl acetate) as hygroscopic crystals.

(Found: C, 47.0; H, 7.1; N, 6.8. C$_{16}$H$_{26}$N$_2$.2HBr requires C, 47.1; H, 6.9; N, 6.9%).

EXAMPLE 26

4-Chloro-5,6,7,8-tetrahydro-7-(N,N - dipropylamino)quinoline

Step 1: 5,6,7,8-tetrahydro-4-nitroquinoline N-oxide

A stirred mixture of sulphuric acid (200 ml) and nitric acid (200 ml) was treated with 5,6,7,8-tetrahydroquinoline N-oxide (47 g, 315 mmol), heated at 60°-80° for 3h, cooled to room temperature, poured onto ice (1 Kg), diluted with water (1 l), and extracted with dichloromethane (3×500 ml). The extracts were dried (MgSO$_4$) and evaporated in vacuo to give the product (48 g) as an oil.

Step 2: 4-chloro-5,6,7,8-tetrahydroquinoline

A solution of the crude product of Step 1 (36.5 g, 188 mmol) in chloroform (500 ml) was treated over 30 min with phosphorus trichloride (80 g, 580 mmol) at 0°, heated under reflux for 1 h, cooled to room temperature, and poured onto ice (2 Kg). The mixture was basified with sodium hydroxide and the layers separated. The aqueous phase was extracted with chloroform (500 ml).

The chlorinated phases were combined, dried (MgSO$_4$), and evaporated in vacuo to give an oil which was purified by chromatography [silica; hexane-ether (2:1)]and distillation to give the product (19 g) as an oil, bp 81°-85°/1 mm Hg.

Step 3: 4-chloro-5,6,7,8-tetrahydro-8-(phenylseleno)-quinoline

A solution of diisopropylamine (18.5 ml, 132 mmol) in tetrahydrofuran (100 ml) at 0° was treated with 1.5M=butyllithium solution in hexane (88 ml, 132 mmol) under A solution of diisopropylamine (18.5 ml, 132 mmol) in tetrahydrofuran (100 ml) at 0° was treated with 1.5M butyllithium solution in hexane (88 ml, 132 mmol) under an atmosphere of nitrogen, stirred for 10 min, cooled to −78°, treated dropwise with the product of Step 2 (7.35 g, 44 mmol) in tetrahydrofuran (50 ml) at <−65°, stirred at −78° for 20 min, treated with phenylselenyl chloride (8.5 g, 44 mmol) in tetrahydrofuran (50 ml), warmed to room temperature, and quenched with saturated aqueous ammonium chloride (250 ml). The reaction was worked-up in a similar way to that described in Example 25, Step ' and the product (9 g) isolated by chromatography [silica; hexane-ether (2:1)] as an oil.

Step 4: 4-chloro-5,6-dihydroquinoline

This compound was prepared from the product of Step 3 (9 g, 28 mmol), 86% 3-chloroperoxybenzoic acid (5.8 g, 29 mmol), and dichloromethane (150 ml) using the procedure outlined in Example 25. Step 2. Distillation gave the product (4.35 g) as an oil.

Step 5: 4-chloro-5,6,7,8-tetrahydro-7-(N-hydroxy-1-propylamino)quinoline

This compound was prepared from the product of Step 4 (4.35 g, 26 mmol), 1-propylhydroxylamine hydrochloride (6 g, 54 mmol), and methanol (10 ml) by the method described in Example 10. The residue was recrystallised from cyclohexane to give the product (5.35 g).

Step 6: 4-chloro-5,6,7,8-tetrahydro-7-(1-propylamino)quinoline

This compound was prepared from the product of Step 5 (5.8 g, 24 mmol) titanium trichloride, 20 wt. % solution in 20 wt. % hydrochloric acid (28 ml, 36 mmol), and methanol (50 ml) using the procedure described in Example 11. The crude amine (5.4 g) was converted directly into the product of Step 7.

Step 7: 4-chloro-N-[7-(5,6,7,8-tetrahydroquinolinyl)]-N-propylpropionamide

This compound was prepared from the crude product of Step 6 (5.4 g, 24 mmol), triethylamine (3.5 ml, 25.2 mmol), propionic anhydride (3.3 ml, 25.7 mmol), and dichloromethane (100 ml) using the way outlined in Example 24, Step 9. The residue was purified by chromatography [alumina; ether-ethyl acetate (2:1)] to give the product (4.1 g) as an oil.

Step 8: 4-chloro-5,6,7,8-tetrahydro-7-(N,N-dipropylamino)quinoline dihydrobromide This compound was prepared from the product of Step 7 (2.9 g, 10.7 mmol) borane-tetrahydrofuran complex, 1M solution in tetrahydrofuran (90 ml), and tetrahydrofuran (20 ml) using the method outlined in Example 24, Step 10, with the exception that the decomposition of the boron-product complex required stirring in 10N-HCl (50 ml) for 18 h. The free base obtained by chromatography [alumina; hexane-ether (2:1)] was dissolved in hot propan-2-ol and the solution acidified with 48% hydrobromic acid. The solution was evaporated in vacuo to give the product as the dihydrobromide (2.6 g), mp 163°–167° (from methanol-ethyl acetate).

(Found: C, 41.8; H, 6.0; N, 6.5. $C_{15}H_{23}ClN_2.2HBr$ requires C, 42.0; H, 5.9; N, 6.5%).

EXAMPLE 27

5,6,7,8-Tetrahydro-4-methoxy-7-(N,N-dipropylaminoquinoline

A solution of sodium methoxide (0.24 g, 10 mmol) and the product free base of Example 26 (0.84 g, 3.1 mmol) in methanol (30 ml) was heated in a sealed vessel at 150° for 16 h, cooled to room temperature, diluted with 0.2M potassium dihydrogen phosphate (pH5) buffer (50 ml), concentrated in vacuo to remove the methanol, washed with ether (3×50 ml) to remove 5,6-dihydro-4-methoxyquinoline side-product, basified with sodium hydroxide, and extracted with dichloromethane (3×50 ml). The extracts were dried $MgSO_4$), and evaporated in vacuo. The free base was dissolved in propan-2-ol (10 ml) and the solution acidified with 48% hydrobromic acid. Evaporation and recrystallisation from methanol-ethyl acetate gave the product as the dihydrobromide hydrate (0.7 g), mp 175°–177°.

(Found: C, 43.4; H, 6.5; N, 6.5. $C_{16}H_{26}N_2O.2HBr.H_{20}$ requires C, 43.5; H, 6.6; N, 6.3%).

EXAMPLE 28

5,6,7,8-Tetrahydro-7-{N-[2-(2,3-dihydro-1,4-benzodioxinyl)]methyl-N-methyl}aminoquinoline A mixture of the product of Example 2 (0.30 g, 1.85 mmol), 2-(2,3-dihydro-1,4-benzodioxinyl)methyl 4-toluenesulphonate (0.71 g, 2.2 mmol), and potassium carbonate (0.30 g, 2.1 mmol) in dimethylformamide (6 ml) was heated at 120° for 6 h, cooled to room temperature, poured into water (20 ml), and extracted with toluene (3×20 ml). The organic phases were extracted with 2N-HCl (2×50 ml) and the acidic extracts basified with sodium hydroxide and extracted with toluene (3×50 ml). The organic extracts were dried ($MgSO_4$) and evaporated in vacuo. The residue was purified by chromatography (silica; methyl acetate) to give two diastereoisomers of the product: the less polar isomer A (0.092 g) and the more polar isomer B (0.102 g).

Isomer A was dissolved in propan-2-ol (2 ml) and the solution acidified with ethereal hydrogen chloride and evaporated in vacuo to give Isomer A dihydrochloride (0.090 g), mp 175°–176°.

(Found: C, 59.3; H, 6.4; N, 7.1. $C_{19}H_{22}N_2O_2.2HCl$ requires C, 59.5; H, 5.8; N, 7.3%).

Isomer B was treated in a similar fashion to give Isomer B dihydrochloride quarter hydrate (0.110 g), mp 173°–174°.

(Found: C, 58.7; H, 6.4; N, 7.0. $C_{19}H_{22}N_2O_2.2HCl.\frac{1}{4}H_2O$ requires C, 58.8; H, 5.8; N, 7.2%).

EXAMPLE 29

N-[7-(5,6,7,8-Tetrahydroquinolinyl)]-N-(1-phenylethyl)hydroxylamine

This compound was prepared from 5,6-dihydroquinoline (20.0 g, 154 mmol), N-(1-phenylethyl)hydroxylamino hydrochloride (26.7 g, 154 mmol), and methanol (400 ml) using the method outlined in Example 1. The crude material was purified by trituration with ether to give the product (22.1 g) as an off-white powder, mp 139°–143°.

EXAMPLE 30

5,6,7,8-Tetrahydro-7-(1-phenylethyl)aminoquinoline

A solution of the hydroxylamine from Example 29 (4.1 g, 17.4 mmol) in 98% sulphuric acid (3.42 g, 34.2 mmol) and acetic acid (65 ml) at 50° was reduced over 10% palladium on carbon (0.3 g) with hydrogen at 40 psi. After 4 h, the mixture was filtered and the filtrate evaporated in vacuo, dissolved in water (50 ml), and basified with 10N-NaOH. The aqueous mixture was extracted with ether (4×30 ml) and the combined organic phases dried ($MgSO_4$), and evaporated in vacuo to give the free base (2.64 g) as a brown oil. The product hydrochloride salt was prepared by conventional means as a white solid, mp 159°–160.5°.

(Found: C, 70.3; H, 7.2; N, 9.8. $C_{17}H_{20}N_2.HCl$ requires C, 70.7; H, 7.3; N, 9.7%).

EXAMPLE 31

7-Amino-5,6,7,8-tetrahydroquinoline

A mixture of the product of Example 30 (5.69 g, 22.6 mmol) and palladium hydroxide (5.69 g) in methanol (150 ml) was shaken under hydrogen at 50 psi for 72 h, filtered and evaporated in vacuo. The crude free base was purified by derivatisation via the N-tert-butyloxycarbonyl derivative: thus the residue was dissolved in dichloromethane (50 ml) and di-tert-butyl dicarbonate (7.0 g, 32.0 mmol) added. The solution was stirred at room temperature for 1 h, concentrated in vacuo, and chromatographed [silica; ethyl acetate-hexane (1:1)] to give 7-(tert-butyloxycarbonylamino)-5,6,7,8-tetrahydroquinoline. The derivative was deprotected by stirring with trifluoroacetic acid for 1 h. Addition of ether produced the product as the di(trifluoroacetate) (3.16 g), mp 141.5°–143.5°.

(Found: C, 41.3; H, 3.7; N, 7.0. $C_9H_{12}N_2.(CF_3CO_2H)_2$ requires C, 41.5; H, 3.7; N, 7.4%).

EXAMPLE 32

N-[7-(5,6,7,8-Tetrahydroquinolinyl)]-N-methylaminoacetonitrile

A solution of the product of Example 2 (11.00 g, 67.9 mmol), chloroacetonitrile (5.13 g, 67.9 mmol), and diisopropylethylamine (8.78 g, 67.9 mmol) in dimethylformamide (100 ml) was stirred at room temperature for 18 h, filtered, and evaporated in vacuo. The residue was dissolved in water (50 ml) and the solution extracted with toluene (3×40 ml). The combined organic phases were extracted with 1N-HCl (3×50 ml). The acidic phases were combined, basified with 5M-KOH, and extracted with toluene (3×50 ml). The combined organic phases were dried ($MgSO_4$), concentrated in vacuo, and chromatographed [silica; hexane-ethyl acetate (1:2 to 0:1)] to afford the free base as a yellow oil.

A solution of the oil in propan-2-ol (20 ml) was acidified with 48% aqueous hydrobromic acid and evaporated in vacuo to give after trituration with ether the product (13.8 g) as the dihydrobromide, off-white crystals, mp 188.5°–191°.

(Found: C, 39.7; H, 4.6; N, 11.5. $C_{12}H_{15}N_3.2HBr$ requires C, 39.7; H, 4.7; N, 11.6%).

EXAMPLE 33

7-[N-(2-Aminoethyl)-N-methyl]amino-5,6,7,8-tetrahydroquinoline

A solution of the product of Example 32 (5.06 g, 25.2 mmol) in saturated ethanolic ammonia (200 ml) was reduced over Raney nickel (1 spatula spoonful) with hydrogen at 50 psi. After 18 h, the mixture was filtered and the filtrate evaporated in vacuo. The brown oil (5.18 g) was used without purification in the synthesis of the compounds of Examples 34 and 35.

EXAMPLE 34

4-Fluoro-N-{2-[N'-(5,6,7,8-tetrahydroquinolin-7-yl)-N'-methyl]aminoethyl}benzamide This compound was prepared from the product of Example 33 (1.30 g, 6.3 mmol), 4-fluorobenzoyl chloride (1.11 g, 7.0 mmol), triethylamine (0.70 g, 6.9 mmol), and dichloromethane (20 ml) by the method described in Example 19. The crude material was purified by chromatography [silica; methanol-ethyl acetate (1:4 to 1:0)] to give an oil. A solution of the free base in ether was treated with hydrogen chloride and the precipitate filtered to give the product (0.25 g) as the dihydrobromide one and a half hydrate, a yellow hygroscopic powder, mp 139°–142°.

(Found: C, 44.6; H, 5.4; N, 7.7. $C_{19}H_{22}FN_3O.2HBr.1\frac{1}{2}H_2O$ requires C, 44.2; H, 5.2; N, 8.1%).

EXAMPLE 35

N-{2-[N'-(5,6,7,8-Tetrahydroquinolin-7-yl)-N'-methyl]aminoethyl}-2,6-difluorophenylacetamide A solution of 2,6-difluorophenylacetic acid (1.15 g, 6.7 mmol) in dioxan (10 ml) was treated with 1,1-carbonyldiimidazole (1.09 g, 6.7 mmol), stirred for 1 h, treated with a solution of the product of Example 33 (1.30 g, 6.3 mmol) and triethylamine (2.22 g, 21.9 mmol) in dioxan (20 ml), stirred for 18 h, and evaporated in vacuo. The oil was dissolved in ethyl acetate (30 ml) and the solution extracted with 1N-HCl (3×30 ml). The acidic layers were combined, basified with 5N-KOH, and extracted with ethyl acetate (3×30 ml). The extracts were washed with brine (20 ml), dried (MgSO$_4$), and evaporated in vacuo. The residue was purified by chromatography [silica; ethyl acetate-methanol (2:1 to 1:1)] to give the product half hydrate (0.97 g) as a brown oil.

(Found: C, 65.0; H, 6.4; N, 1.9. $C_{20}H_{23}F_2N_3O.\frac{1}{2}H_2O$) requires C, 65.3; H, 6.6; N, 11.4%).

EXAMPLE 36

5,6,7,8-Tetrahydro-7-(phenylamino)quinoline

Glacial acetic acid (1.2 ml, 20 mmol) was added dropwise to a stirred solution of 5,6-dihydroquinoline (1.31 g, 10 mmol) and aniline (1.86 g, 20 mmol) in methanol (4 ml). The solution was heated under reflux for 21 h, cooled to room temperature, poured onto a mixture of saturated aqueous sodium chloride (25 ml) and water (25 ml), and the mixture was basified with 10N-NaOH and extracted with ether (3×25 ml). The extracts were concentrated in vacuo to give a dark orange oil which was chromatographed [alumina; ethyl acetate-toluene (1:24 to 1:4)] to give a solid. Recrystallisation from di-isopropyl ether gave the product (1 50 g), mp 102°–103°.

(Found: C, 80.4; H, 7.2; N, 12.5. $C_{15}H_{16}N_2$ requires C, 80.3; H, 7.2; N, 12.5%).

EXAMPLE 37

5,6,7,8-Tetrahydro-7-piperidinoquinoline

This compound was prepared from acetic acid (1.2 ml, 20 mmol), 5,6-dihydroquinoline (1.31 g, 10 mmol), and piperidine (1.71 g, 20 mmol) using the method described in Example 36 and a reaction time of 67 h. The crude oil was purified by chromatography [alumina; ethyl acetate-toluene (1:4)]. A solution of the free base in ethyl acetate was acidified with ethereal hydrogen chloride and concentrated in vacuo. The pale orange gum was crystallised from isopropanol-tetrahydrofuran (1:2) and the solid triturated with acetonitrile to give the product as the dihydrochloride (0.66 g), mp 169°–170°.

(Found: C, 58.2; H, 7.8; N, 10.0. $C_{14}H_{20}N_2.2HCl$ requires C, 58.15; H, 7.65; N, 9.7%).

EXAMPLE 38

5,6,7,8-Tetrahydro-7-pyrrolidinoquinoline

This compound was prepared from acetic acid (1.2 ml, 20 mmol), 5,6-dihydroquinoline (1.31 g, 10 mmol), and pyrrolidine (1.42 g, 20 mmol) using the method described in Example 36. The crude oil was purified by chromatography [alumina; ethyl acetate-toluene (1:19 to 1:4)]. A solution of the free base in ethyl acetate was acidified with ethereal hydrogen chloride, concentrated in vacuo, and crystallisation induced with isopropanol. The solid was triturated with acetonitrile to give the product as the dihydrochloride (1.42 g), mp 165°–167°.

(Found: C, 56.4; H, 7.6; N, 9.95. $C_{13}H_{18}N_2.2HCl$ requires C, 56.75; H, 7.3; N, 10.2%).

EXAMPLE 39

5,6,7,8-Tetrahydro-7-morpholinoquinoline

This compound was prepared from acetic acid (1.2 ml, 20 mmol), 5,6-dihydroquinoline (1.31 g, 10 mmol), and morpholine (1.74 g, 20 mmol) using the method described in Example 36 and chloroform instead of ether as the extracting solvent. The crude oil was purified by chromatography [alumina; ethyl acetate-toluene (1:19 to 2:3)]. A solution of the free base in ethyl acetate was acidified with ethereal hydrogen chloride, concentrated in vacuo, and crystallisation induced with ethanol. The solid was triturated with acetonitrile to give the product as the dihydrochloride, quarter hydrate (1.83 g), mp 166°–168°.

(Found: C, 53.15; H, 6.9; N, 9.4. $C_{13}H_{18}N_2O.2HCl.0.25H_2O$ requires C, 52.9; H, 7.0; N, 9.5%).

EXAMPLE 40

5,6,7,8-Tetrahydro 7-{1-[4-(2-methoxyphenyl)piperazinyl]}quinoline

This compound was prepared from acetic acid (0.6 ml, 10 mmol), 1-(2-methoxyphenyl)piperazine (1.92 g, 10 mmol), and 5,6-dihydroquinoline (1.31 g, 10 mmol) using the method described in Example 36 except that the reaction time was 44 h and the extracting solvent was ethyl acetate. The crude oil was purified by chromatography alumina; ethyl acetate-toluene (1:19 to 2:3)]. The free base was dissolved in ethyl acetate and the solution acidified with ethereal hydrogen chloride and concentrated in vacuo. The solid was triturated with acetonitrile to give the product as the trihydrochloride, half hydrate (1.82 g), mp 180°–186°.

(Found: C, 54.6; H, 6.45; N, 9.5. $C_{20}H_{25}N_3O.3HCl.0.5H_2O$ requires C, 54.35; H, 6.6; N, 9.5%).

EXAMPLE 41

5,6,7,8-Tetrahydro-7-(phenylmethylamino)quinoline

This compound was prepared from acetic acid (1.2 ml, 20 mmol), 5,6-dihydroquinoline (1.31 g, 10 mmol), and benzylamine (2.14 g, 20 mmol) using the method described in Example 36. The crude oil was purified by chromatography [alumina; ethyl acetate-toluene (1:19 to 2:3)]. The free base was dissolved in ethyl acetate and the solution acidified with ethereal hydrogen chloride and concentrated in vacuo. The solid was triturated with acetonitrile to give the product as the dihydrochloride (1.60 g), mp 181°–185°.

(Found: C 61.45; H, 6.8; N, 9.0. $C_{16}H_{18}N_2.2HCl$ requires C, 61.75; H, 6.5; N, 9.0%).

EXAMPLE 42

2,3-Dihydro-N-[7-(5,6,7,8-tetrahydroquinolinyl)]-1,4-benzodioxin-2-carboxamide

A solution of 2,3-dihydro-1,4-benzodioxin-2-carboxylic acid (1.20 g, 6.65 mmol) and 1,1-carbonyldiimidazole (1.08 g, 6.65 mmol) in acetonitrile (20 ml) was stirred at room temperature for 40 min, treated with a solution of the di(trifluoroacetate) salt of the amine of Example 31 (2.50 g, 6.65 mmol) and triethylamine (0.67 g, 6.65 mmol) in acetonitrile (70 ml), and after 18 h evaporated in vacuo. The residue was dissolved in ethyl acetate (50 ml) and the solution extracted with 1N-HCl (2×25 ml). The combined acidic phases were basified with 5N-KOH and extracted with ethyl acetate (3×30 ml). The combined organic phases were washed with brine (30 ml) and water (30 ml), dried (MgSO$_4$), and concentrated in vacuo to afford a gum which was chromatographed (silica; ethyl acetate) to give the product (1.94 g) as a colourless foam which was converted into the amine of Example 45.

EXAMPLE 43

Piperazine-1,4-bis[7,7'-(5,6,7,8-tetrahydroquinoline)]

This compound was prepared from acetic acid (1.2 ml, 20 mmol), piperazine (1.72 g, 20 mmol), and 5,6-dihydroquinoline (1.31 g, 10 mmol) using the method described in Example 36 except that the reaction time was 40 h and the extracting solvent was chloroform. The crude oil was purified by chromatography (alumina; ethyl acetate) to give a solid which was recrystallised from ethyl acetate to give the product as the hydrate (0.18 g), mp 163°–167°.

(Found: C, 72.35; H, 8.2; N, 15.35. $C_{22}H_{28}N_4.H_2O$ requires C, 72.1; H, 8.25; N, 15.3%).

EXAMPLE 44

5,6,7,8-Tetrahydro-7-[1-(4-phenylmethyl)piperazinyl]-quinoline

This compound was made from acetic acid (0.6 ml, 10 mmol), 5,6-dihydroquinoline (1.31 g, 10 mmol), and 1-(phenylmethyl)piperazine (1.72 g, 10 mmol) using the method described in Example 43. The crude oil was purified by chromatography [alumina; ethyl acetate-toluene (1:9 to 2:3)]. The free base was dissolved in ethyl acetate and the solution was acidified with ethereal hydrogen chloride. The mixture was concentrated in vacuo, dissolved in methanol, concentrated in vacuo and triturated with acetonitrile to give the product as the trihydrochloride, hydrate (1.70 g), mp 155° (dec).

(Found: C, 54.9; H, 7.05; N, 9.45. $C_{20}H_{25}N_3.3HCl.H_2O$ requires C, 55.2; H, 6.95; N, 9.7%).

EXAMPLE 45

5,6,7,8-Tetrahydro-7-[2-(2,3-dihydro-1,4-benzodioxinyl)methylamino]quinoline

Borane-methyl sulphide complex (2 ml, 20 mmol) was added dropwise to a solution of the product of Example 2 (2.07 g, 6.68 mmol) in tetrahydrofuran (20 ml) and the solution was heated under reflux for 18 h cooled to −10°, treated dropwise with methanol (5 ml), evaporated in vacuo, treated with methanol (20 ml), evaporated in vacuo, and treated with water (10 ml) and 10N-HCl (10 ml). The aqueous suspension was heated under reflux for 30 min, concentrated in vacuo, and the foam dissolved in water (20 ml). The solution was basified with 5N-KOH and extracted with ethyl acetate (3×30 ml). The extracts were washed with brine (30 ml) and water (30 ml), dried (MgSO$_4$), and concentrated in vacuo. The residue was chromatographed [silica; ethyl acetate→ethyl acetate-methanol (3:1)] to afford an oil which was dissolved in ethanol. The solution was acidified with ethereal hydrogen chloride and the precipitate filtered to give the dihydrochloride salt of the product (1.15 g), mp 171°–174°.

(Found: C, 58.1; H, 6.2; N, 7.4. $C_{18}H_{20}N_2O_2.2HCl$ requires C, 8.5; H, 6.0; N, 7.6%).

EXAMPLE 46

7-Amino-5,6,7,8-tetrahydroquinoline

This compound was prepared from ammonium acetate (1.54 g, 20 mmol) and 5,6-dihydroquinoline (2.31 g, 10 mmol) using the method described in Example 36 and ethyl acetate instead of ether as the extracting solvent.

The crude oil was chromatographed [alumina; ethyl acetate-toluene (1:4)→ethyl acetate] to give the product (0.179 g) as an oil which was identical to the compound isolated as the di(trifluoroacetate) in Example 31.

EXAMPLE 47

5,6,7,8-Tetrahydro-7-(1-propylamino)quinoline

This compound was prepared from acetic acid (1.2 ml, 20 mmol), 5,6-dihydroquinoline (1.31 g, 10 mmol) and propylamine (1.19 g, 20 mmol) by the method described in Example 36 except that the reaction time was 64 h and the extracting solvent was ethyl acetate instead of ether. The crude oil was chromatographed [alumina; ethyl acetate-toluene (1:19 to 2:3)] to give the product (0.905 g) as an oil which was identical to the compound isolated in Example 11.

EXAMPLE 48

5,6,7,8-Tetrahydro-7-(methylamino)quinoline

A solution of methylammonium chloride (1.35 g, 20 mmol) in methanol (2 ml) was added to 5,6-dihydroquinoline (1.31 g, 10 mmol) in methanol (2 ml) and the solution was heated under reflux for 21 h, poured onto a mixture of water (25 ml) and brine (25 ml), and basified with 10N-NaOH (25 ml). The mixture was extracted with chloroform (3×25 ml), and the extracts were dried ($Na_2SO_4$) and concentrated in vacuo to give an orange oil. Chromatography [alumina; ethyl acetate-toluene (1:4)→ethyl acetate] gave the product (1.35 g) as an oil which was identical to the compound isolated in Example 2.

EXAMPLE 49

5,6,7,8-Tetrahydro-7-dimethylaminoquinoline

This compound was prepared from dimethylammonium chloride (1.63 g, 20 mmol) and 5,6-dihydroquinoline (1.31 g, 10 mmol) using the experimental and purification method describes in Example 48. The product (0.72 g) was an oil which was identical to the compound isolated in Example 3.

EXAMPLE 50

7-Azetidino-5,6,7,8-tetrahydroquinoline

This compound was prepared from acetic acid (1.2 ml, 20 mmol), 5,6-dihydroquinoline (1.31 g, 10.0 mmol), and azetidine (1.25 g, 21.9 mmol) using the method described in Example 39. The crude oil was purified by chromatography [alumina; ethyl acetate-toluene (1:9 to 2:3)]. A solution of the free base in ethyl acetate was acidified with ethereal hydrogen chloride and evaporated in vacuo. The solid was triturated with acetonitrile to give the product as the dihydrochloride hemihydrate (0.95 g), mp 120°–122°.

(Found: C, 53.3; H, 7.3; N, 10.35. $C_{12}H_{16}N_2.2HCl.\frac{1}{2}H_2O$ requires C, 53.3; H, 7.1; N, 10.4%).

EXAMPLE 51

Resolution of 7-azetidino-5,6,7,8-tetrahydroquinoline

The free base of the compound of Example 50 (6.60 g, 35.1 mmol) in hot acetone (50 ml) was treated with a hot solution of (-)-dibenzoyl-L-tartaric acid monohydrate (13.17 g, 35.0 mmol) in acetone (530 ml) and the solution allowed to cool for 21 h. The precipitate was removed by filtration, suspended in a mixture of water (200 ml) and chloroform (200 ml), and the mixture basified with 5N-NaOH (20 ml). The layers were separated and the aqueous phase extracted with chloroform (50 ml). The extract was concentrated in vacuo, acetonitrile (100 ml) was added, and the solution was concentrated in vacuo. The product was once more subjected to the resolution procedure just described to afford the free base of the first enantiomer (1.50 g),$[\alpha]_D$ at 24° C.=−55.5° (c 1.1 in $CHCl_3$). The product was dissolved in methanol (75 ml), and the solution was acidified with ethereal hydrogen chloride (5 ml), and concentrated in vacuo. The residue was crystallised by trituration with acetonitrile (10 ml) to give the first enantiomer as the dihydrochloride quarter hydrate (1.66 g), mp 126°–128° C.

(Found: C, 54.3; H, 7.1: N, 10.5. $C_{12}H_{16}N_2$. 2HCl. 0.25 $H_2O$ requires C, 54.25; H, 7.0; N, 10.5%);$[\alpha]_D$ at 24° C.=−74.7° (c 1.15 in $H_2O$).

The mother liquors from the above resolution were converted to the free base (4.98 g, 26.5 mmol). This was subjected to the resolution procedure just described but using (+)-dibenzoyl-D-tartaric acid monohydrate as the chiral acid. The free base of the second enantiomer $[\alpha]_D$ at 24° C.=+59.4° (c 1.1 in $CHCl_3$) was converted to the dihydrochloride quarter hydrate (1.56 g), mp 120°–131° C.

(Found: C, 54.1; H, 7.0; N, 10.6. $C_{12}H_{16}N_2$. 2HCl. 0.25 $H_2O$ requires C, 54.25; H, 7.0; N, 10.5%); $[\alpha]_D$ at 24° C.=+71.2° (c 1.05 in $H_2O$).

We claim:

1. A compound of formula

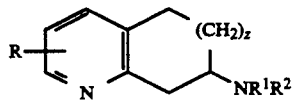

or the heteroaromatic N-oxide thereof or a pharmaceutically acceptable acid addition salt thereof, in which z is 0, 1 or 2;

R is hydrogen, hydroxy, lower alkyl, lower alkoxy, halogen, trifluoromethyl, nitro, amino, (lower)alkylamino or di(lower)alkylamino;

$R^1$ is hydrogen or lower alkyl and $R^2$ is —$(CH_2)_n$—$R^3$ or —$CH_2$—CH=CH—$(CH_2)_m$—$R^3$ or —$CH_2.C≡C.(CH_2)_m$—$R^3$ where n is 1 to 6, and m is 0 to 3 and $R^3$ is a ring of formula

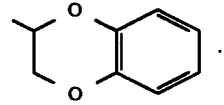

2. A compound as claimed in claim 1 which is 5,6,7,8-Tetrahydro-7-[N-[2-(2,3-dihydro-1,4-benzodioxinyl]-methyl-N-propyl]aminoquinoline; 7-Amino-5,6,7,8-tetrahydro-N-[2-[2-(2,3-dihydro-1,4-benzodioxinyl)]ethyl]-N-methylquinoline; 5,6,7,8-Tetrahydro-7-[N-[2-(2,3-dihydro-1,4-benzodioxinyl)methyl-N-methyl-]aminoquinoline; or 5,6,7,8-Tetrahydro-7-[2-(2,3-dihydro-1,4-benzodioxinyl)methylamino]quinoline or a pharmaceutically acceptable acid addition salt thereof.

3. A pharmaceutical composition comprising a compound claimed in claim 1 in association with a pharmaceutically acceptable carrier.

* * * * *